United States Patent [19]

Alsop

[11] 4,005,984
[45] Feb. 1, 1977

[54] DIAGNOSTIC COMPOSITION AND METHOD OF USING THE SAME

[76] Inventor: Reese Fell Alsop, Lloyd Lane, Lloyd Neck, Huntington, N.Y. 11743

[22] Filed: Feb. 17, 1976

[21] Appl. No.: 658,550

Related U.S. Application Data

[63] Continuation-in-part of Ser. No. 578,771, May 16, 1975, abandoned.

[52] U.S. Cl. .............................. 23/230 B; 128/2 W; 252/408
[51] Int. Cl.² ........................................ G01N 33/16
[58] Field of Search .................. 23/230 B, 253 TP; 128/2 W

[56] References Cited

FOREIGN PATENTS OR APPLICATIONS 1,018,563  1/1966  United Kingdom .............. 128/2 W Primary Examiner—R.E. Serwin
Attorney, Agent, or Firm—Nolte and Nolte

[57] ABSTRACT

A diagnostic composition comprising a mixture of a lubricant and chemical reagents for the detection of occult blood components in stools is inserted through the anus into the rectum and removed, whereby there is carried with the composition a specimen of stool.

9 Claims, No Drawings

DIAGNOSTIC COMPOSITION AND METHOD OF USING THE SAME

This is a continuation-in-part of application Ser. No. 578,771, filed May 16, 1975, and now abandoned.

This invention relates to a diagnostic composition and to the method of using the diagnostic composition. More particularly, the diagnostic composition is for the detection of occult blood in stools.

In the examination of living animals, particularly humans, the detection of occult blood in the stool has long been known to be an indication for further x-ray studies and proctoscopic examination. It has been conservatively estimated that reliable detection of occult blood in the stool can increase the early diagnosis of carcinoma of the colon, a curable cancer, by at least 20%.

Heretofore, the examination of stools for the presence of occult blood has required the patient or the doctor to collect a stool specimen whereupon the doctor has the specimen submitted to a sequence of chemical tests or manipulations, all of which is obviously inconvenient.

According to the present invention, chemical reagents for the detection of occult blood in stools is admixed with a lubricant. The lubricant selected is one, such as petroleum jelly, Surgilube (Trademark of Day Baldwin, Inc, Hillside, New Jersey) lubricating jelly, KY (trademark of Johnson and Johnson, New Brunswick, New Jersey) lubricating jelly and the like, which would normally be used by a physician conducting a rectal examination to permit insertion of his finger or an implement through the anus into the rectum. When the finger or implement carrying the composition of the invention is withdrawn from the rectum, it inevitably carries with it a specimen of stool. Hence, in the normal course of a rectal examination, there is obtained a specimen of stool in contact or admixed with a composition containing chemical reagents for the detection of occult blood. These reagents within a matter of seconds to three minutes automatically cause a change in color of the composition on the examining finger if blood is present, thus eliminating any need for further steps or processing.

More specifically, preferred chemical reagents for the detection of occult blood in stools are guaiac together with glacial acetic acid and hydrogen peroxide. These reagents are mixed with the petroleum jelly or other lubricant in the proportion of about 5 to about 10 parts by weight of reagents per 100 parts by weight of petroleum jelly or other lubricant. A sufficient quantity of the mixture, typically about 5 to 6 grams, to permit insertion of the physician's finger or implement into the rectum through the anus is applied to the finger or the implement and then withdrawn carrying with it the composition and a specimen of stool which turns blue either immediately or within about three minutes if blood is present.

In summary, an old, well-known combination of reagents consisting of a saturated solution of guaiac together with hydrogen peroxide and glacial acetic acid (Bray's Clinical Laboratory Methods, 7th Edition, page 452) is mixed with a lubricant in proportions, by weight, of the reagents to the lubricant of about one or two to twenty. The resulting admixture then indicates the presence of blood products on contact with any specimen of blood-containing stool. By incorporating the indicator into the lubricant, every examination of the rectum must, of necessity, include a test for occult blood.

Alternatively, like proportions of other conventional combinations of reagents for the detection of occult blood in stools can be incorporated in a lubricant and used in accordance with the present invention. These other known conventional reagent systems include, for example, a saturated solution of benzidine dihydrochloride in glacial acetic acid, guaiac with a peroxide other than hydrogen peroxide, such as barium peroxide and with or without an acid material, and o-tolidine together with a peroxide and with or without an acid material.

A further important discovery, as an offshoot of the above work, relates to the chemical stability of the combination of reagents. Particularly in the case of the guaiac, instead of rapid deterioration in a matter of hours by oxygen in room air, as is usual, it was found that when the lubricant was added to the reagents, it protected the viability of the mixture. Thus, the end product remained diagnostically effective for as long as three months. The addition of the lubricant, therefore, constitutes a new method for producing a stable, long-acting system for the detection of occult blood in physical diagnosis.

What is claimed is:
1. A diagnostic composition for the detection of occult blood in stools consisting essentially of an intimate mixture of chemical reagents selected from the group consisting of guaiac, glacial acetic acid, hydrogen peroxide, barium peroxide, benzidine dihydrochloride, and o-tolidine and a lubricant.

2. A diagnostic composition according to claim 1 in which the lubricant is petroleum jelly.

3. A diagnostic composition according to claim 1, in which the chemical reagents are a mixture of guaiac, hydrogen peroxide and glacial acetic acid.

4. A diagnostic composition according to claim 1, in which the chemical reagents are a mixture of guaiac and barium peroxide.

5. A diagnostic composition according to claim 1, in which the chemical reagents are a combination of o-tolidine and hydrogen peroxide.

6. A diagnostic composition according to claim 1, in which the chemical reagents are a saturated solution of benzidine dihydrochloride in a saturated solution of glacial acetic acid.

7. A method of detecting occult blood in stools, comprising inserting the composition according to claim 1 through the anus into the rectum and removing the composition carrying therewith a specimen of stool.

8. A method of detecting occult blood in stools, comprising inserting the composition according to claim 2 through the anus into the rectum and removing the composition carrying therewith a specimen of stool.

9. A method of detecting occult blood in stools, comprising inserting the composition according to claim 6 through the anus into the rectum and removing the composition carrying therewith a specimen of stool.

* * * * *